(12) United States Patent
Linger et al.

(10) Patent No.: US 9,701,991 B2
(45) Date of Patent: Jul. 11, 2017

(54) METHODS FOR CELLOBIOSAN UTILIZATION

(71) Applicant: Alliance for Sustainable Energy, LLC, Golden, CO (US)

(72) Inventors: Jeffrey Linger, Denver, CO (US); Gregg T. Beckham, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/063,197

(22) Filed: Mar. 7, 2016

(65) Prior Publication Data

US 2016/0257980 A1    Sep. 8, 2016

Related U.S. Application Data

(60) Provisional application No. 62/129,384, filed on Mar. 6, 2015.

(51) Int. Cl.
| | |
|---|---|
| *C12N 9/42* | (2006.01) |
| *C12P 19/14* | (2006.01) |
| *C12P 19/02* | (2006.01) |
| *C13K 13/00* | (2006.01) |

(52) U.S. Cl.
CPC ............ *C12P 19/02* (2013.01); *C12N 9/2445* (2013.01); *C12P 19/14* (2013.01); *C13K 13/00* (2013.01)

(58) Field of Classification Search
None
See application file for complete search history.

(56) References Cited

U.S. PATENT DOCUMENTS 4,952,501 A    8/1990   Jasin et al.

OTHER PUBLICATIONS

Dai et al., "Cloning of a novel levoglucosan kinase gene from *Lipomyces starkeyi* and its expression in *Escherichia coli*", World Journal of Microbiology & Biotechnology, 2009, vol. 25, pp. 1589-1595.
Lian et al., "Separation, Hydrolysis and Fermentation of Pyrolytic Sugars to Produce Ethanol and Lipids", Bioresource Technology, 2010, vol. 101, No. 24, pp. 9688-9699.
Linger et al., "Conversion of Levoglucosan and Cellobiosan by *Pseudomonas putida* KT2440", Metabolic Engineering Communications, 2016, vol. 3, pp. 24-29.
Pollard et al., "Characterization of Bio-oil Recovered as Stage Fractions with Unique Chemical and Physical Properties", Journal of Analytical and Applied Pyrolysis, Jan. 2012, vol. 93, pp. 129-138.
Rover et al., "Production of Clean Pyrolytic Sugars for Fermentation", ChemSusChem, Jun. 2014, vol. 7, No. 6, pp. 1662-1668.
Seidle et al., "Physical and Kinetic Properties of the Family 3 β-Glucosidase from *Aspergillus niger* which is Important for Cellulose Breakdown", The Protein Journal, Jan. 2004, vol. 23, No. 1, pp. 11-23.

*Primary Examiner* — Yong Pak
(74) *Attorney, Agent, or Firm* — John C. Stolpa

(57) ABSTRACT

Disclosed herein are enzymes useful for the degradation of cellobiosan in materials such a pyrolysis oils. Methods of degrading cellobiosan using enzymes or organisms expressing the same are also disclosed.

20 Claims, 8 Drawing Sheets

A.

B.

C.

SEQUENCE LISTING

```
<160> NUMBER OF SEQ ID NOS: 6

<210> SEQ ID NO 1
<211> LENGTH: 1317
<212> TYPE: DNA
<213> ORGANISM: Lipomyces starkeyi
<220> FEATURE:
<221> NAME/KEY: CDS
<222> LOCATION: (1)..(1317)

<400> SEQUENCE: 1 atg ccc att gct act tcc acg ggc gat aac gtt ttg gat ttc aca gtt      48
Met Pro Ile Ala Thr Ser Thr Gly Asp Asn Val Leu Asp Phe Thr Val
1               5                   10                  15 ttg ggg ttg aac tca gga acc tca atg gac ggt atc gat tgt gcg ctg      96
Leu Gly Leu Asn Ser Gly Thr Ser Met Asp Gly Ile Asp Cys Ala Leu
            20                  25                  30 tgt cac ttc tat cag aaa act ccg gac gca ccg atg gag ttt gaa ctg     144
Cys His Phe Tyr Gln Lys Thr Pro Asp Ala Pro Met Glu Phe Glu Leu
        35                  40                  45 ctg gaa tac ggg gag gtt ccc ctg gct cag cca att aag caa cgt gta     192
Leu Glu Tyr Gly Glu Val Pro Leu Ala Gln Pro Ile Lys Gln Arg Val
    50                  55                  60 atg cgg atg att tta gag gat act acg tct ccg agc gaa ctg tct gaa     240
Met Arg Met Ile Leu Glu Asp Thr Thr Ser Pro Ser Glu Leu Ser Glu
65                  70                  75                  80 gtt aac gtt atc ctg ggc gaa cac ttt gcc gat gca gta cgt cag ttc     288
Val Asn Val Ile Leu Gly Glu His Phe Ala Asp Ala Val Arg Gln Phe
                85                  90                  95 gcc gca gaa agg aac gtc gat ttg tca acg att gat gca atc gct agc     336
Ala Ala Glu Arg Asn Val Asp Leu Ser Thr Ile Asp Ala Ile Ala Ser
            100                 105                 110 cat gga caa acg atc tgg ttg ctg tcc atg ccg gag gag ggt cag gtg     384
```

-continued

```
                His Gly Gln Thr Ile Trp Leu Leu Ser Met Pro Glu Gly Gln Val
                            115                 120                 125 aaa tcc gca cta aca atg gcc gaa ggc gcc att ctg gcc tct cgt acg         432
Lys Ser Ala Leu Thr Met Ala Glu Gly Ala Ile Leu Ala Ser Arg Thr
            130                 135                 140 gga ata acc tca att act gat ttt aga att tca gat caa gca gct ggc         480
Gly Ile Thr Ser Ile Thr Asp Phe Arg Ile Ser Asp Gln Ala Ala Gly
145                 150                 155                 160 cgt cag ggg gcc ccc ctg att gca ttc ttc gac gcg cta ctc ctg cat         528
Arg Gln Gly Ala Pro Leu Ile Ala Phe Phe Asp Ala Leu Leu Leu His
                165                 170                 175 cac cca acg aag tta aga gct tgt cag aac ata ggt gga att gca aac         576
His Pro Thr Lys Leu Arg Ala Cys Gln Asn Ile Gly Gly Ile Ala Asn
            180                 185                 190 gta tgc ttc att cca cca gat gtt gat ggg cgc cgg act gat gaa tat         624
Val Cys Phe Ile Pro Pro Asp Val Asp Gly Arg Arg Thr Asp Glu Tyr
        195                 200                 205 tat gac ttt gac aca ggt cca ggc aac gtc ttt att gac gcg gtg gtt         672
Tyr Asp Phe Asp Thr Gly Pro Gly Asn Val Phe Ile Asp Ala Val Val
210                 215                 220 cgc cat ttc acg aac ggc gaa cag gaa tat gat aag gac ggg gcg atg         720
Arg His Phe Thr Asn Gly Glu Gln Glu Tyr Asp Lys Asp Gly Ala Met
225                 230                 235                 240 ggc aag cgc ggg aaa gtg gat cag gag ctt gtg gat gac ttt ttg aaa         768
Gly Lys Arg Gly Lys Val Asp Gln Glu Leu Val Asp Asp Phe Leu Lys
                245                 250                 255 atg cct tac ttt cag ctt gat cca cct aaa acc aca ggc cgt gaa gtg         816
Met Pro Tyr Phe Gln Leu Asp Pro Pro Lys Thr Thr Gly Arg Glu Val
            260                 265                 270 ttt agg gat aca ttg gca cat gat ttg atc aga cgc gca gaa gct aaa         864
Phe Arg Asp Thr Leu Ala His Asp Leu Ile Arg Arg Ala Glu Ala Lys
        275                 280                 285 ggg ctg tcc ccg gac gac ata gta gct acc acc act cgc ata act gcc         912
Gly Leu Ser Pro Asp Asp Ile Val Ala Thr Thr Thr Arg Ile Thr Ala
290                 295                 300 caa gca att gtg gat cat tat cgt cgc tat gct ccc agt cag gaa atc         960
Gln Ala Ile Val Asp His Tyr Arg Arg Tyr Ala Pro Ser Gln Glu Ile
305                 310                 315                 320 gat gaa att ttt atg tgc ggt ggc gga gcc tac aac ccg aac atc gtt        1008
Asp Glu Ile Phe Met Cys Gly Gly Gly Ala Tyr Asn Pro Asn Ile Val
                325                 330                 335 gag ttt att cag cag tcg tac ccc aat acc aag att atg atg cta gac        1056
Glu Phe Ile Gln Gln Ser Tyr Pro Asn Thr Lys Ile Met Met Leu Asp
            340                 345                 350 gag gcg ggc gta ccg gcg ggg gcc aaa gaa gcc atc act ttc gcg tgg        1104
Glu Ala Gly Val Pro Ala Gly Ala Lys Glu Ala Ile Thr Phe Ala Trp
        355                 360                 365 cag ggc atg gag gca ctg gtg ggg cgt tcg atc cca gtc ccg acc cgc        1152
Gln Gly Met Glu Ala Leu Val Gly Arg Ser Ile Pro Val Pro Thr Arg
370                 375                 380 gtg gaa acc cgc cag cat tac gtt ctg ggt aag gtg tct cca ggc cta        1200
Val Glu Thr Arg Gln His Tyr Val Leu Gly Lys Val Ser Pro Gly Leu
385                 390                 395                 400 aat tac cgc tcc gta atg aaa aag ggc atg gct ttt gga gga gat gca        1248
Asn Tyr Arg Ser Val Met Lys Lys Gly Met Ala Phe Gly Gly Asp Ala
                405                 410                 415 caa caa ctc ccc tgg gtg agc gaa atg att gtc aaa aaa aaa ggt aaa        1296
Gln Gln Leu Pro Trp Val Ser Glu Met Ile Val Lys Lys Lys Gly Lys
            420                 425                 430
```

```
gtg att acc aat aat tgg gcc                                          1317
Val Ile Thr Asn Asn Trp Ala
        435

<210> SEQ ID NO 2
<211> LENGTH: 439
<212> TYPE: PRT
<213> ORGANISM: Lipomyces starkeyi

<400> SEQUENCE: 2

Met Pro Ile Ala Thr Ser Thr Gly Asp Asn Val Leu Asp Phe Thr Val
1               5                   10                  15

Leu Gly Leu Asn Ser Gly Thr Ser Met Asp Gly Ile Asp Cys Ala Leu
            20                  25                  30

Cys His Phe Tyr Gln Lys Thr Pro Asp Ala Pro Met Glu Phe Glu Leu
        35                  40                  45

Leu Glu Tyr Gly Glu Val Pro Leu Ala Gln Pro Ile Lys Gln Arg Val
    50                  55                  60

Met Arg Met Ile Leu Glu Asp Thr Thr Ser Pro Ser Glu Leu Ser Glu
65                  70                  75                  80

Val Asn Val Ile Leu Gly Glu His Phe Ala Asp Ala Val Arg Gln Phe
                85                  90                  95

Ala Ala Glu Arg Asn Val Asp Leu Ser Thr Ile Asp Ala Ile Ala Ser
            100                 105                 110

His Gly Gln Thr Ile Trp Leu Leu Ser Met Pro Glu Glu Gly Gln Val
        115                 120                 125

Lys Ser Ala Leu Thr Met Ala Glu Gly Ala Ile Leu Ala Ser Arg Thr
130                 135                 140

Gly Ile Thr Ser Ile Thr Asp Phe Arg Ile Ser Asp Gln Ala Ala Gly
145                 150                 155                 160

Arg Gln Gly Ala Pro Leu Ile Ala Phe Phe Asp Ala Leu Leu Leu His
                165                 170                 175

His Pro Thr Lys Leu Arg Ala Cys Gln Asn Ile Gly Gly Ile Ala Asn
            180                 185                 190

Val Cys Phe Ile Pro Pro Asp Val Asp Gly Arg Arg Thr Asp Glu Tyr
        195                 200                 205

Tyr Asp Phe Asp Thr Gly Pro Gly Asn Val Phe Ile Asp Ala Val Val
    210                 215                 220

Arg His Phe Thr Asn Gly Glu Gln Glu Tyr Asp Lys Asp Gly Ala Met
225                 230                 235                 240

Gly Lys Arg Gly Lys Val Asp Gln Glu Leu Val Asp Asp Phe Leu Lys
                245                 250                 255

Met Pro Tyr Phe Gln Leu Asp Pro Pro Lys Thr Thr Gly Arg Glu Val
            260                 265                 270

Phe Arg Asp Thr Leu Ala His Asp Leu Ile Arg Arg Ala Glu Ala Lys
        275                 280                 285

Gly Leu Ser Pro Asp Asp Ile Val Ala Thr Thr Thr Arg Ile Thr Ala
    290                 295                 300

Gln Ala Ile Val Asp His Tyr Arg Arg Tyr Ala Pro Ser Gln Glu Ile
305                 310                 315                 320

Asp Glu Ile Phe Met Cys Gly Gly Gly Ala Tyr Asn Pro Asn Ile Val
                325                 330                 335

Glu Phe Ile Gln Gln Ser Tyr Pro Asn Thr Lys Ile Met Met Leu Asp
            340                 345                 350

Glu Ala Gly Val Pro Ala Gly Ala Lys Glu Ala Ile Thr Phe Ala Trp
```

355                 360                 365
Gln Gly Met Glu Ala Leu Val Gly Arg Ser Ile Pro Val Pro Thr Arg
        370                 375                 380
Val Glu Thr Arg Gln His Tyr Val Leu Gly Lys Val Ser Pro Gly Leu
385                 390                 395                 400
Asn Tyr Arg Ser Val Met Lys Lys Gly Met Ala Phe Gly Gly Asp Ala
                405                 410                 415
Gln Gln Leu Pro Trp Val Ser Glu Met Ile Val Lys Lys Lys Gly Lys
        420                 425                 430
Val Ile Thr Asn Asn Trp Ala
        435

<210> SEQ ID NO 3
<211> LENGTH: 860
<212> TYPE: PRT
<213> ORGANISM: Aspergillus niger

<400> SEQUENCE: 3

Met Arg Phe Thr Leu Ile Glu Ala Val Ala Leu Thr Ala Val Ser Leu
1               5                   10                  15
Ala Ser Ala Asp Glu Leu Ala Tyr Ser Pro Tyr Tyr Pro Ser Pro
            20                  25                  30
Trp Ala Asn Gly Gln Gly Asp Trp Ala Gln Ala Tyr Gln Arg Ala Val
        35                  40                  45
Asp Ile Val Ser Gln Met Thr Leu Asp Glu Lys Val Asn Leu Thr Thr
    50                  55                  60
Gly Thr Gly Trp Glu Leu Glu Leu Cys Val Gly Gln Thr Gly Gly Val
65                  70                  75                  80
Pro Arg Leu Gly Val Pro Gly Met Cys Leu Gln Asp Ser Pro Leu Gly
                85                  90                  95
Val Arg Asp Ser Asp Tyr Asn Ser Ala Phe Pro Ala Gly Met Asn Val
            100                 105                 110
Ala Ala Thr Trp Asp Lys Asn Leu Ala Tyr Leu Arg Gly Lys Ala Met
        115                 120                 125
Gly Gln Glu Phe Ser Asp Lys Gly Ala Asp Ile Gln Leu Gly Pro Ala
    130                 135                 140
Ala Gly Pro Leu Gly Arg Ser Pro Asp Gly Gly Arg Asn Trp Glu Gly
145                 150                 155                 160
Phe Ser Pro Asp Pro Ala Leu Ser Gly Val Leu Phe Ala Glu Thr Ile
                165                 170                 175
Lys Gly Ile Gln Asp Ala Gly Val Val Ala Thr Ala Lys His Tyr Ile
            180                 185                 190
Ala Tyr Glu Gln Glu His Phe Arg Gln Ala Pro Glu Ala Gln Gly Phe
        195                 200                 205
Gly Phe Asn Ile Ser Glu Ser Gly Ser Ala Asn Leu Asp Asp Lys Thr
    210                 215                 220
Met His Glu Leu Tyr Leu Trp Pro Phe Ala Asp Ala Ile Arg Ala Gly
225                 230                 235                 240
Ala Gly Ala Val Met Cys Ser Tyr Asn Gln Ile Asn Asn Ser Tyr Gly
                245                 250                 255
Cys Gln Asn Ser Tyr Thr Leu Asn Lys Leu Leu Lys Ala Glu Leu Gly
            260                 265                 270
Phe Gln Gly Phe Val Met Ser Asp Trp Ala Ala His His Ala Gly Val
        275                 280                 285

```
Ser Gly Ala Leu Ala Gly Leu Asp Met Ser Met Pro Gly Asp Val Asp
            290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
                340                 345                 350

Pro Asn Phe Ser Ser Trp Thr Arg Asp Glu Tyr Gly Tyr Lys Tyr Tyr
            355                 360                 365

Tyr Val Ser Glu Gly Pro Tyr Glu Lys Val Asn Gln Tyr Val Asn Val
370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
                420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Val Thr Pro Glu Gln
450                 455                 460

Ala Ile Ser Asn Glu Val Leu His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
                500                 505                 510

Asn Val Asp Gly Asn Leu Gly Asp Arg Arg Asn Leu Thr Leu Trp Arg
            515                 520                 525

Asn Gly Asp Asn Val Ile Lys Ala Ala Ser Asn Cys Asn Asn Thr
530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
            595                 600                 605

Asp Tyr Leu Val Thr Glu Pro Asn Asn Gly Asn Gly Ala Pro Gln Glu
610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
                660                 665                 670

Glu Pro Ala Ser Gly Glu Thr Glu Ala Ala Pro Thr Phe Gly Glu Val
            675                 680                 685

Gly Asn Ala Ser Asp Tyr Leu Tyr Pro Ser Gly Leu Gln Arg Ile Thr
690                 695                 700

Lys Phe Ile Tyr Pro Trp Leu Asn Gly Thr Asp Leu Glu Ala Ser Ser
```

```
                705                 710                 715                 720
        Gly Asp Ala Ser Tyr Gly Gln Asp Ser Ser Asp Tyr Leu Pro Glu Gly
                        725                 730                 735

Ala Thr Asp Gly Ser Ala Gln Pro Ile Leu Pro Ala Gly Gly Gly Pro
                        740                 745                 750

Gly Gly Asn Pro Arg Leu Tyr Asp Glu Leu Ile Arg Val Ser Val Thr
                        755                 760                 765

Ile Lys Asn Thr Gly Lys Val Ala Gly Asp Glu Val Pro Gln Leu Tyr
                        770                 775                 780

Val Ser Leu Gly Gly Pro Asn Glu Pro Lys Ile Val Leu Arg Gln Phe
        785                 790                 795                 800

Glu Arg Ile Thr Leu Gln Pro Ser Glu Glu Thr Lys Trp Ser Thr Thr
                        805                 810                 815

Leu Thr Arg Arg Asp Leu Ala Asn Trp Asn Val Glu Lys Gln Asp Trp
                        820                 825                 830

Glu Ile Thr Ser Tyr Pro Lys Met Val Phe Val Gly Ser Ser Arg
                        835                 840                 845

Lys Leu Pro Leu Arg Ala Ser Leu Pro Thr Val His
                        850                 855                 860

<210> SEQ ID NO 4
<211> LENGTH: 823
<212> TYPE: PRT
<213> ORGANISM: Phanerochaete chrysosporium

<400> SEQUENCE: 4

Met Gly Leu Thr Leu Val Val Leu Leu His Leu Ala Leu Gly Leu Leu
        1               5                   10                  15

Thr Gly Val Gln Ala Gln Ser Gly Leu Tyr Gln Gln Cys Gly Gly Ile
                        20                  25                  30

Gly Trp Thr Gly Ala Thr Thr Cys Val Ser Gly Ala Thr Cys Thr Val
                        35                  40                  45

Leu Asn Pro Tyr Tyr Ser Gln Cys Leu Pro Gly Ala Ala Thr Thr Ser
                        50                  55                  60

Val Ser Ser Ser His Ser Ser Ser Ser Val Ser Ser His Ser Ser
        65                  70                  75                  80

Ser Ala Ser Ser Ser Ser Ile Ser Ser Thr Thr Ser Pro Ala
                        85                  90                  95

Pro Ser Gln Thr Val Ala Asn Val Ser Pro Glu Trp Ala Ala Ala Tyr
                        100                 105                 110

Val Lys Ala Gln Ala Ala Val Ala Lys Leu Ser Val Thr Asp Met Val
                        115                 120                 125

Asn Leu Ala Thr Gly Val Gln Trp Gln Lys Gly Pro Cys Val Gly Asn
                        130                 135                 140

Thr Pro Ala Ile Ser Ser Ile Pro Gly Phe Thr Gly Leu Cys Leu Gln
        145                 150                 155                 160

Asp Ser Pro Val Gly Val Arg Tyr Ala Asp Gly Thr Ser Val Phe Pro
                        165                 170                 175

Pro Glu Ile Asn Val Ala Ala Thr Trp Asn Arg Thr Leu Met Arg Gln
                        180                 185                 190

Arg Gly Ala Ala Met Gly Ala Glu Phe Lys Gly Lys Gly Val His Val
                        195                 200                 205

Ala Leu Gly Pro Met Met Asn Leu Met Arg Val Pro Ala Ala Gly Arg
                        210                 215                 220
```

-continued

```
Asn Trp Glu Gly Gly Gly Asp Pro Phe Leu Ser Gly Glu Val Ala
225                 230                 235                 240

Phe Glu Thr Ile Thr Gly Ile Gln Ser Ser Gly Ala Gln Ala Cys Ala
            245                 250                 255

Lys His Phe Ile Asn Asn Glu Gln Glu His Phe Arg Asp Ser Ser Ser
                260                 265                 270

Ser Asn Val Asp Asp Arg Thr Glu His Glu Leu Tyr Gly His Pro Phe
        275                 280                 285

Leu Arg Ser Val Gln Ala Asn Val Ala Ser Val Met Cys Ser Tyr Asn
    290                 295                 300

Gln Ile Asn Gly Thr Phe Ser Cys Glu Asn Glu Lys Thr Leu Ser Gly
305                 310                 315                 320

Leu Leu Lys Gly Glu Tyr Gly Phe Gln Gly Tyr Val Met Ser Asp Trp
                325                 330                 335

Trp Ala Thr His Ser Gly Ala Pro Ala Val Asn Ala Gly Leu Asp Met
                340                 345                 350

Thr Met Pro Gly Asp Glu Thr Leu Ser Ser Gly Thr Thr Tyr Phe Gly
            355                 360                 365

Gln Asn Leu Val Asn Ala Val Asn Ser Gly Gln Val Ser Gln Ala Arg
370                 375                 380

Val Lys Asp Met Ala Thr Arg Ile Leu Ala Ala Trp Tyr Leu Leu Gly
385                 390                 395                 400

Gln Asp Gln Asn Phe Pro Ala Val Asn Phe Asn Ser Trp Asn Ser Gly
                405                 410                 415

Gln Gly Gln His Val Asn Val Ser Gly Asn His Ala Ser Leu Ile Arg
                420                 425                 430

Thr Ile Gly Ala Ala Ser Gln Ile Leu Leu Lys Asn Val Asn Ser Ala
            435                 440                 445

Leu Pro Leu Lys Lys Pro Lys Thr Ile Gly Ile Ile Gly Asn Gly Ala
450                 455                 460

Gly Ser Asn Pro Asn Gly Pro Asn Ala Phe Ser Asp Arg Ala Gly Asp
465                 470                 475                 480

Val Gly Val Leu Ala Leu Gly Trp Gly Ser Gly Thr Ala Asn Phe Pro
                485                 490                 495

Tyr Leu Val Ala Pro Val Asp Ala Ile Thr Ala Arg Ala Ser Gln Asp
            500                 505                 510

Gly Thr Thr Val Ser Ser Ser Leu Ser Asp Thr Asp Leu Thr Gly Ala
            515                 520                 525

Ala Asn Thr Ala Thr Gly Lys Asp Val Ala Met Val Phe Ile Thr Ala
530                 535                 540

Asp Ser Gly Glu Gly Tyr Leu Thr Val Glu Gly Asn Ala Gly Asp Arg
545                 550                 555                 560

Asn Asp Leu Gln Ala Trp His Gly Gly Asp Ala Leu Val Gln Gln Val
                565                 570                 575

Ala Ser His Asn Lys Asn Thr Ile Val Val Ile Asn Ser Val Gly Pro
            580                 585                 590

Ile Asn Met Glu Ala Trp Val Asn His Pro Asn Val Thr Ala Ile Val
            595                 600                 605

Trp Ser Gly Leu Pro Gly Gln Glu Ala Gly Asn Ala Val Thr Asp Val
610                 615                 620

Leu Phe Gly Ala Val Asn Pro Gly Gly Lys Leu Pro Phe Thr Ile Gly
625                 630                 635                 640

Lys Ser Ile Ser Asp Tyr Ser Ala Gln Ile Ile Thr Thr Gly Ser Gly
```

```
                    645                 650                 655
Ile Val Pro Ile Pro Tyr Asn Glu Gly Leu Phe Ile Asp Tyr Arg His
                660                 665                 670

Phe Asp Gln Ala Gly Ile Ala Pro Arg Phe Glu Phe Gly Phe Gly Leu
            675                 680                 685

Ser Tyr Thr Thr Phe Asp Tyr Ser Asn Leu Val Ile Thr Gly Ser Thr
690                 695                 700

Ala Gly Gly Thr Arg Gln Pro Gly Pro Gly Ser Ser Leu Asp Pro
705                 710                 715                 720

Trp Leu His Asp Ser Val Val Thr Val Ser Phe Thr Leu Thr Asn Asn
                725                 730                 735

Gly Thr Val Asp Gly Thr Glu Val Pro Gln Leu Tyr Leu Ser Pro Pro
                740                 745                 750

Ala Ser Ala Lys Ser Ala Pro Gln Asn Leu Lys Gly Phe Asp Ser Val
            755                 760                 765

Phe Leu Pro Ala Gly Ala Ser Thr Thr Val Ser Phe Glu Leu Ser Arg
770                 775                 780

Tyr Ser Phe Ser Val Trp Asp Val Val Ser Gln Ser Trp Gln Ile Pro
785                 790                 795                 800

Ala Gly Val Thr Gly Ile Ser Val Gly Ala Ser Ser Arg Asp Leu Arg
                805                 810                 815

Leu Lys Gly Ser Ile Thr Asn
            820

<210> SEQ ID NO 5
<211> LENGTH: 446
<212> TYPE: PRT
<213> ORGANISM: Thermotoga maritima

<400> SEQUENCE: 5

Met Asn Val Lys Lys Phe Pro Glu Gly Phe Leu Trp Gly Val Ala Thr
1               5                   10                  15

Ala Ser Tyr Gln Ile Glu Gly Ser Pro Leu Ala Asp Gly Ala Gly Met
            20                  25                  30

Ser Ile Trp His Thr Phe Ser His Thr Pro Gly Asn Val Lys Asn Gly
        35                  40                  45

Asp Thr Gly Asp Val Ala Cys Asp His Tyr Asn Arg Trp Lys Glu Asp
    50                  55                  60

Ile Glu Ile Ile Glu Lys Leu Gly Val Lys Ala Tyr Arg Phe Ser Ile
65                  70                  75                  80

Ser Trp Pro Arg Ile Leu Pro Glu Gly Thr Gly Arg Val Asn Gln Lys
                85                  90                  95

Gly Leu Asp Phe Tyr Asn Arg Ile Ile Asp Thr Leu Leu Glu Lys Gly
            100                 105                 110

Ile Thr Pro Phe Val Thr Ile Tyr His Trp Asp Leu Pro Phe Ala Leu
        115                 120                 125

Gln Leu Lys Gly Gly Trp Ala Asn Arg Glu Ile Ala Asp Trp Phe Ala
    130                 135                 140

Glu Tyr Ser Arg Val Leu Phe Glu Asn Phe Gly Asp Arg Val Lys Asn
145                 150                 155                 160

Trp Ile Thr Leu Asn Glu Pro Trp Val Val Ala Ile Val Gly His Leu
                165                 170                 175

Tyr Gly Val His Ala Pro Gly Met Arg Asp Ile Tyr Val Ala Phe Arg
            180                 185                 190
```

```
Ala Val His Asn Leu Leu Arg Ala His Ala Arg Ala Val Lys Val Phe
        195                 200                 205
Arg Glu Thr Val Lys Asp Gly Lys Ile Gly Ile Val Phe Asn Asn Gly
    210                 215                 220
Tyr Phe Glu Pro Ala Ser Glu Lys Glu Asp Ile Arg Ala Val Arg
225                 230                 235                 240
Phe Met His Gln Phe Asn Asn Tyr Pro Leu Phe Leu Asn Pro Ile Tyr
                245                 250                 255
Arg Gly Asp Tyr Pro Glu Leu Val Leu Glu Phe Ala Arg Glu Tyr Leu
            260                 265                 270
Pro Glu Asn Tyr Lys Asp Met Ser Glu Ile Gln Glu Lys Ile Asp
        275                 280                 285
Phe Val Gly Leu Asn Tyr Tyr Ser Gly His Leu Val Lys Phe Asp Pro
        290                 295                 300
Asp Ala Pro Ala Lys Val Ser Phe Val Glu Arg Asp Leu Pro Lys Thr
305                 310                 315                 320
Ala Met Gly Trp Glu Ile Val Pro Glu Gly Ile Tyr Trp Ile Leu Lys
                325                 330                 335
Lys Val Lys Glu Glu Tyr Asn Pro Pro Glu Val Tyr Ile Thr Glu Asn
            340                 345                 350
Gly Ala Ala Phe Asp Asp Val Val Ser Glu Asp Gly Arg Val His Asp
            355                 360                 365
Gln Asn Arg Ile Asp Tyr Leu Lys Ala His Ile Gly Gln Ala Trp Lys
        370                 375                 380
Ala Ile Gln Glu Gly Val Pro Leu Lys Gly Tyr Phe Val Trp Ser Leu
385                 390                 395                 400
Leu Asp Asn Phe Glu Trp Ala Glu Gly Tyr Ser Lys Arg Phe Gly Ile
                405                 410                 415
Val Tyr Val Asp Tyr Ser Thr Gln Lys Arg Ile Val Lys Asp Ser Gly
            420                 425                 430
Tyr Trp Tyr Ser Asn Val Val Lys Asn Asn Gly Leu Glu Asp
        435                 440                 445

<210> SEQ ID NO 6
<211> LENGTH: 459
<212> TYPE: PRT
<213> ORGANISM: Agrobacterium sp.

<400> SEQUENCE: 6

Met Thr Asp Pro Asn Thr Leu Ala Ala Arg Phe Pro Gly Asp Phe Leu
1               5                   10                  15
Phe Gly Val Ala Thr Ala Ser Phe Gln Ile Glu Gly Ser Thr Lys Ala
                20                  25                  30
Asp Gly Arg Lys Pro Ser Ile Trp Asp Ala Phe Cys Asn Met Pro Gly
            35                  40                  45
His Val Phe Gly Arg His Asn Gly Asp Ile Ala Cys Asp His Tyr Asn
        50                  55                  60
Arg Trp Glu Glu Asp Leu Asp Leu Ile Lys Glu Met Gly Val Glu Ala
65                  70                  75                  80
Tyr Arg Phe Ser Leu Ala Trp Pro Arg Ile Ile Pro Asp Gly Phe Gly
                85                  90                  95
```

```
Pro Ile Asn Glu Lys Gly Leu Asp Phe Tyr Asp Arg Leu Val Asp Gly
            100                 105                 110

Cys Lys Ala Arg Gly Ile Lys Thr Tyr Ala Thr Leu Tyr His Trp Asp
            115                 120                 125

Leu Pro Leu Thr Leu Met Gly Asp Gly Gly Trp Ala Ser Arg Ser Thr
130                 135                 140

Ala His Ala Phe Gln Arg Tyr Ala Lys Thr Val Met Ala Arg Leu Gly
145                 150                 155                 160

Asp Arg Leu Asp Ala Val Ala Thr Phe Asn Glu Pro Trp Cys Ala Val
                165                 170                 175

Trp Leu Ser His Leu Tyr Gly Val His Ala Pro Gly Glu Arg Asn Met
                180                 185                 190

Glu Ala Ala Leu Ala Ala Met His His Ile Asn Leu Ala His Gly Phe
                195                 200                 205

Gly Val Glu Ala Ser Arg His Val Ala Pro Lys Val Pro Val Gly Leu
    210                 215                 220

Val Leu Asn Ala His Ser Ala Ile Pro Ala Ser Asp Gly Glu Ala Asp
225                 230                 235                 240

Leu Lys Ala Ala Glu Arg Ala Phe Gln Phe His Asn Gly Ala Phe Phe
                245                 250                 255

Asp Pro Val Phe Lys Gly Glu Tyr Pro Ala Glu Met Met Glu Ala Leu
                260                 265                 270

Gly Asp Arg Met Pro Val Val Glu Ala Glu Asp Leu Gly Ile Ile Ser
            275                 280                 285

Gln Lys Leu Asp Trp Trp Gly Leu Asn Tyr Tyr Thr Pro Met Arg Val
            290                 295                 300

Ala Asp Asp Ala Thr Pro Gly Val Glu Phe Pro Ala Thr Met Pro Ala
305                 310                 315                 320

Pro Ala Val Ser Asp Val Lys Thr Asp Ile Gly Trp Glu Val Tyr Ala
                325                 330                 335

Pro Ala Leu His Thr Leu Val Glu Thr Leu Tyr Glu Arg Tyr Asp Leu
                340                 345                 350

Pro Glu Cys Tyr Ile Thr Glu Asn Gly Ala Cys Tyr Asn Met Gly Val
                355                 360                 365

Glu Asn Gly Gln Val Asn Asp Gln Pro Arg Leu Asp Tyr Tyr Ala Glu
            370                 375                 380

His Leu Gly Ile Val Ala Asp Leu Ile Arg Asp Gly Tyr Pro Met Arg
385                 390                 395                 400

Gly Tyr Phe Ala Trp Ser Leu Met Asp Asn Phe Glu Trp Ala Glu Gly
                405                 410                 415

Tyr Arg Met Arg Phe Gly Leu Val His Val Asp Tyr Gln Thr Gln Val
                420                 425                 430

Arg Thr Val Lys Asn Ser Gly Lys Trp Tyr Ser Ala Leu Ala Ser Gly
            435                 440                 445

Phe Pro Lys Gly Asn His Gly Val Ala Lys Gly
450                 455
```

METHODS FOR CELLOBIOSAN UTILIZATION

CROSS-REFERENCE TO RELATED APPLICATIONS

This application claims priority to U.S. Provisional Application No. 62/129,384, filed Mar. 6, 2015, the contents of which are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "14-71_ST25.txt," having a size in bytes of 36 kb and created on Mar. 7, 2016. Pursuant to 37 CFR §1.52(e)(5), the information contained in the above electronic file is hereby incorporated by reference in its entirety.

BACKGROUND

Thermal processes for biomass deconstruction, such as pyrolysis and liquefaction, offer rapid, effective methods for the depolymerization of plant cell wall components. These processes typically produce heterogeneous slates of compounds derived from polysaccharides and lignin that can potentially be upgraded simultaneously over chemical catalysts, integrated into petroleum refinery streams, or fractionated through a wide variety of approaches and subsequently upgraded in a more selective manner to a broader slate of fuels and chemicals. Cellobiosan, or 1,6-anhydro-β-D-glucose, is a major component of pyrolysis oil derived from cellulose and hemicellulose.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide methods for degrading cellobiosan by contacting a cellobiosan-containing material with an enzyme capable of hydrolyzing β-1,4-glycosidic bonds to generate levoglucosan. In some embodiments, the enzyme comprises a Glycoside Hydrolase (GH) domain selected from the Glycoside Hydrolase Families GH1, GH3, GH5, GH9, GH30 or GH116.

In certain embodiments, the enzyme is a β-glucosidase or endoglucanase, such as a β-glucosidase or endoglucanase from a bacterium or fungus. In some embodiments, the bacterium is from the genus *Agrobacterium* (e.g., *Agrobacterium* sp.) or *Thermotoga* (e.g., *Thermotoga maritima*). In others, the fungus is from the genus *Aspergillus* (e.g., *A. niger*) or *Phanerochaete* (e.g., *P. chrysosporium*).

In various embodiments, the β-glucosidase is *Agrobacterium* sp. abg, *Thermotoga maritima* bglA, *Aspergillus niger* bgl1, or *Phanerochaete chrysosporium* bgl1A.

In some embodiments, the cellobiosan-containing material is a pyrolysis oil, such as an oil derived from the pyrolysis of biomass, or a fraction obtained by fractionating a pyrolysis oil (e.g., an aqueous fraction).

In certain embodiments, the enzyme is expressed by a microorganism and the cellobiosan containing material is contacted with the microorganism to degrade the cellobiosan. In various embodiments, the microorganism expresses an exogenous gene encoding a levoglucosan kinase, such as the levoglucosan kinase LGK from *Lipomyces starkeyi*.

In some embodiments, the microorganism is a bacterium, such as a bacterium from the genus *Pseudomonas* (e.g., *P. putida*). In further embodiments, an exogenous β-glucosidase may also be added to degrade the cellobiosan.

Additional exemplary embodiments provide methods for producing levoglucosan and glucose from cellobiosan by contacting the cellobiosan with at least one β-glucosidase and isolating at least one of the levoglucosan or glucose products.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

Disclosed herein are enzymes (and organisms expressing these enzymes) useful for the more efficient utilization of saccharides such as those found in pyrolysis oil. Methods of biologically cleaving cellobiosan found in feedstocks such as pyrolysis oil or fractions thereof into monosaccharides are also disclosed.

Pyrolysis offers a straightforward approach for the deconstruction of plant cell wall polymers into pyrolysis oil or bio-oil, which may be fractionated and subsequently used in biological approaches to selectively upgrade some of the resulting fractions. An exemplary pyrolysis set-up is demonstrated in FIG. 8. One fraction of interest for biological upgrading contains polysaccharide-derived substrates including sugars and sugar dehydration products such as levoglucosan and cellobiosan, which are two of the most abundant pyrolysis products of cellulose. To date, however, the biological utilization of cellobiosan has not been demonstrated. Rather, cellobiosan is typically hydrolyzed to glucose by treatment with a strong acid such as sulfuric acid ($H_2SO_4$).

In typical fast pyrolysis schemes, levoglucosan and cellobiosan are the most abundantly produced dehydration products of cellulose. Cellobiosan has been identified as a major component of anhydrosugars from the pyrolysis of Avicel (between 6-15% of the liquid product). The only utilization of cellobiosan and larger anhydrosugar oligomers derived from cellulose has been observed when acid hydrolysis is combined with subsequent conversion of the glucose (after hydrolysis of the glycosidic bonds for depolymerization and hydrolysis of levoglucosan to produce glucose).

Multiple tandem catalytic-biological schemes have been developed to fractionate levoglucosan-rich streams from bio-oil, hydrolyze it to glucose, and upgrade it to, for example, ethanol. For example, Lian et al., *Bioresource Technology* 101:9688-9699 (2010) demonstrate a fractionation process that used solvent fractionation to separate phenolics from pyrolytic sugars, hydrolyze the levoglucosan to glucose, and then use a biological step to either produce ethanol or fatty acids.

The selective fractionation of pyrolysis-derived substrates and use of biological approaches to selectively upgrade at least some of the resulting fractions are attractive as a means for efficient utilization of bio-oils. Given the high concentration of cellobiosan in pyrolysis oil, identifying a mechanism enabling the metabolic utilization of this compound is paramount to biological upgrading of pyrolysis oils. The present work represents a move towards a consolidated biological step for production of fuels or chemicals from pyrolytic sugar streams.

Figure 1:
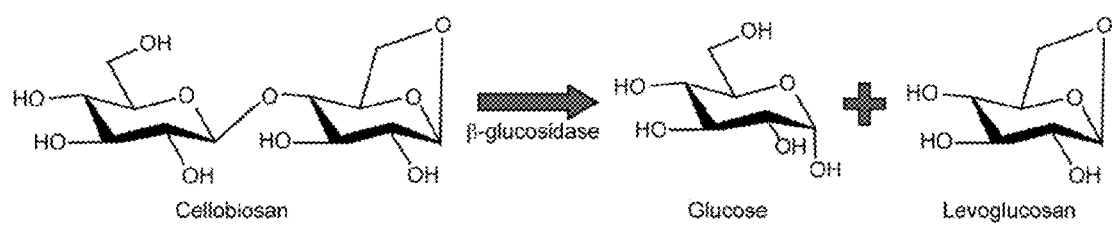
FIG. 1 shows a mechanism for cellobiosan cleavage via an exemplary enzyme disclosed herein to generate glucose and levoglucosan.

Cellobiosan-containing materials may be contacted with enzymes disclosed herein to degrade the cellobiosan to levoglucosan and glucose. A major component of the aqueous fraction of pyrolysis oil is cellobiosan, which consists of a disaccharide wherein the reducing end has undergone a dehydration reaction to form a levoglucosan connected to glucose. In order to derive value from the aqueous phase of pyrolysis oil, one route would be to biologically metabolize the primary components—including cellobiosan—to generate higher-value products. An exemplary reaction scheme utilizing a β-glucosidase to cleave cellobiosan into levoglucosan and glucose is provided in FIG. 1.

Disclosed herein are methods of converting cellobiosan to levoglucosan and glucose with enzymes capable of cleaving the β-1,4-glycosidic bond in cellobiosan to liberate glucose and levoglucosan. Exemplary enzymes with this catalytic activity include β-glucosidases and endoglucanases. Being able to convert cellobiosan into its monomeric units enables the biological utilization of cellobiosan and enables the production of endless bio-products. Previously there were no known routes for the biological utilization of cellobiosan.

Suitable enzymes include those from Glycoside Hydrolase (GH) families 1, 3, 5, 9, 30, or 116. Exemplary enzymes also include those comprising a GH1 domain, a GH3 domain, a GH5 domain, a GH9 domain, a GH30 domain or a GH116 domain. Specific enzymes containing these GH domains are listed in the CAZY (Carbohydrate-Active enZYmes) database, grouped by GH family and available on the internet. Further examples include *Bacillus thuringiensis* GH5, *Thermoanaerobacterium xylanolyticum* GH116, *Homo sapiens* GH30, *Mus musculus* GH30 and *Phytophthora infestans* GH30.

Enzymes possessing a Glycoside Hydrolase Family 1 domain or a Glycoside Hydrolase Family 3 domain are typically referred to as β-glucosidases, which have previously not been shown to be active of cellobiosan substrates.

As used herein, "cellobiosan-containing materials" means any natural or processed materials comprising detectable amounts of cellobiosan. These may be derived from many sources, including oils derived from the pyrolysis of biomass of other lignocellulose or cellulose sources. Exemplary materials with high cellobiosan content include pyrolysis oil, bio-oil, fast pyrolysis oil and fractions thereof. Various fractions of pyrolysis oils may be obtained by, for example, extractions of the oils using various aqueous or organic solvents, or other processing steps. Also suitable are other sources of anhydrosugars, including cellobiosan in purified or semi-purified form. While use of pyrolysis oils is exemplified here, any source of cellobiosan may be suitable for use with the methods herein, including cellobiosan derived from liquefaction or other high temperature methods to break down cellulose.

The Examples below demonstrate that β-glucosidases are capable of hydrolyzing the β-1,4-glycosidic bond in cellobiosan to liberate glucose and levoglucosan as products. While β-glucosidases are exemplified, additional enzymes disclosed herein (including endoglucanases) are suitable for use in the methods. β-glucosidases from many families may be used to degrade cellobiosan. Generally, enzymes with the ability to cleave β-1,4-glycosidic bonds (such as those containing a Glycoside Hydrolase (GH) Family 1 (GH1) domain or GH Family 3 (GH3) domain) are suitable for use in the methods disclosed herein. In various embodiments, the enzyme is a GH1 family enzyme, a GH3 family enzyme, a β-glucosidase, an endoglucanase, or combinations thereof.

Suitable enzymes may be derived from both prokaryotic and eukaryotic organisms, or from mesophilic, thermophilic or hyperthermophilic organisms. Enzymes may be derived from microorganisms such as bacteria, fungi, yeast or the like via cell lysis and isolation techniques, or produced recombinantly. Additional enzymes include any enzyme able to cleave β-1,4-glycosidic bonds, regardless of species. For example, β-glucosidases are highly conserved across diverse biological organisms, from bacteria to higher eukaryotes such as mice and humans. Suitable enzymes may be from the kingdoms/domains Bacteria, Archaea or Eucarya.

In some embodiments, a microorganism expressing the enzyme may be used to directly as a biocatalyst to degrade the cellobiosan sample. Exemplary bacteria include those from the genera *Agrobacterium* (e.g., *Agrobacterium* sp.) and *Thermotoga* (e.g., *T. maritima*), while exemplary fungi include those from the genera *Aspergillus* (e.g., *A. niger, A. nidulans, A. awamori,* or *A. aculeatus*) and *Phanerochaete* (e.g., *P. chrysosporium*). Other species of the genus *Ther-*

*motoga* include *T. elfii, T. hypogeal, T. lettingae, T. naphthophila, T. neapolitana, T. petrophila, T. subterranean,* and *T. thermarum.*

Enzymes described herein may be used as purified recombinant enzyme or as culture broths from cells that naturally produce the enzyme or that have been engineered to produce the enzyme. β-Glucosidases or endoglucanases can be added exogenously, or may be expressed and secreted directly from a microbial biocatalyst. In some embodiments, the enzymes may be expressed in a bacterium from the genus *Pseudomonas,* such as *P. putida* or a strain thereof such as *P. putida* KT2440. Additional host organisms include those disclosed below.

Certain embodiments disclosed herein involve microorganisms that have been genetically modified to express a gene encoding levoglucosan kinase (LGK). The amino acid sequence of LGK from *Lipomyces starkeyi* can be found at GenBank Accession No. EU751287 and SEQ ID NO:2. Additional examples of levoglucosan kinases are known in the art, including the microbial examples found in Dai et al., *World J Microbiol Biotechnol* 25:1589-1595 (2009).

Levoglucosan can be converted to glucose-6-phosphate (G6P) through the activity of a LGK. Expression of exogenous LGK by a microorganism allows the microbe to more fully utilize levoglucosan present in a feedstock, including levoglucosan derived from cellobiosan as described herein. An exemplary LGK enzyme is the lgk gene from *Lipomyces starkeyi,* which is active for conversion of levoglucosan to G6P. The lgk gene may be expressed in microbial biocatalysts such as *P. putida* KT2440 (see Example 1).

The addition of β-glucosidase or endoglucanase to an LGK strain of *P. putida* KT2440, for example, enables complete utilization of cellobiosan via hydrolytic cleavage of the glycosidic linkage, liberating glucose and levoglucosan. β-glucosidases or endoglucanases can be added exogenously or may be expressed and secreted directly from the microbial biocatalyst.

Hybrid processing requires biocatalysts that span the breadth of molecules present in thermochemical-derived substrates as well as detoxification strategies that enable growth of a given biocatalyst. *P. putida* KT2440 represents a promising strain for hybrid processing applications given its inherent ability to tolerate toxic environments, the ability to engineer the microbe, and the large suite of endogenous substrate specificity beyond sugars especially for aromatic catabolism. Strains of *P. putida* may be engineered to catabolize a broad range of substrates including xylose and phenol, among others. *P. putida* strains may also be engineered to express exogenous levoglucosan kinase, thereby enabling the utilization of levoglucosan from biomass-derived feedstocks, including thermochemical-derived substrates and lignin-derived streams. In addition, microbes such as *Rhodococcus jostii* RHA1, *Acinetobacter* sp. ADP1, and *Amycolatopsis* sp. may be similarly engineered and used as biocatalysts.

Bio-oils and other cellobiosan-containing materials may be contacted with enzymes at a concentration and a temperature for a time sufficient to achieve the desired amount of cellobiosan degradation. The enzymes disclosed herein may be used at any temperature, but may also well suited for higher temperature digestions. For example, the enzymes or cocktails may be used at temperatures ranging from about 30° C. to about 100° C., or from about 40° C. to about 80° C., or from about 50° C. to about 65° C., depending on the thermophilic nature of the enzyme Suitable times for cellobiosan degradation range from a few hours to several days, and may be selected to achieve a desired amount of degradation. Exemplary digestion times include 1, 2, 3, 4, 5, 6, 7, 8, 9, 10, 11, or 12 hours; and 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 days. In some embodiments, digestion times may be one or more weeks.

The resulting products after cellobiosan degradation may also be converted to products such as ethanol via fermentation or upgraded to products other than ethanol. Examples include conversion to higher alcohols, hydrocarbons, or other advanced fuels via biological or chemical pathways, or combination thereof. Products (such as levoglucosan or glucose) may be recovered or isolated from the cellobiosan degradation reactions by standard separation techniques for further upgrading. Products may also be further processed by a biocatalyst into additional fuels or chemicals.

Cellulose containing materials may be subjected to pyrolysis processes to generate oils rich in cellobiosan. Exemplary cellulose-containing materials include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure.

Table 1 below provides GenBank accession numbers for the nucleic acid and amino acid sequences for exemplary β-glucosidases for use in the disclosed methods. "Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases. Also included are cDNA molecules.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having protein activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional β-glucosidase or endoglucanase. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

Embodiments of the nucleic acids include those that encode the polypeptides that functions as β-glucosidases, endoglucanases or functional equivalents thereof. A functional equivalent includes fragments or variants of these that exhibit the ability to function as a β-glucosidase or endoglucanase. As a result of the degeneracy of the genetic code, many nucleic acid sequences can encode a given polypeptide with a particular enzymatic activity. Such functionally equivalent variants are contemplated herein.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*, filamentous fungi from the genera *Trichoderma* (e.g., *T. reesei, T. viride, T. koningii*, or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A. awamori*, or *A. aculeatus*), *Fusarium, Neurospora, Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, miscanthus, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from filamentous fungi by direct transformation, in which DNA is mixed with the cells and taken up without any additional manipulation, by conjugation, electroporation, or other means known in the art. Expression vectors may be expressed by filamentous fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing filamentous fungi, for example, are available from ATCC. Exemplary culture/fermentation conditions and reagents are provided in the Examples that follow.

The nucleic acid molecules described herein encode the enzymes with amino acid sequences such as those represented by Table 1. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented in Table 1, or may include up to a certain integer number of amino acid alterations. Such protein or polypeptide variants retain functionality as β-glucosidases or endoglucanases, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences set forth in Table 1 and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

EXAMPLES

Example 1

Plasmid and Strain Construction and Levoglucosan Utilization

The levoglucosan kinase (lgk) gene from *Lipomyces starkeyi* was codon optimized using Gene Designer software from DNA 2.0 and synthesized as a gBlock (SEQ ID NO:1). This fragment was cloned into plasmid pMFL76, which is derived from the commercial PCR-Blunt II Topo vector (ThermoFisher), with the addition of two 1-kb genomic regions located in proximity of the rpoS region of the genome from *Pseudomonas putida* KT2440 to enable homologous recombination mediated genomic integration into strain KT2440. The Ptac-lgk was inserted in between these 1 kb homology regions and transformed into KT2440. A single kanamycin-resistant transformant was isolated and growth in M9 levoglucosan was confirmed, to generate strain FJPO3.

Figure 2:
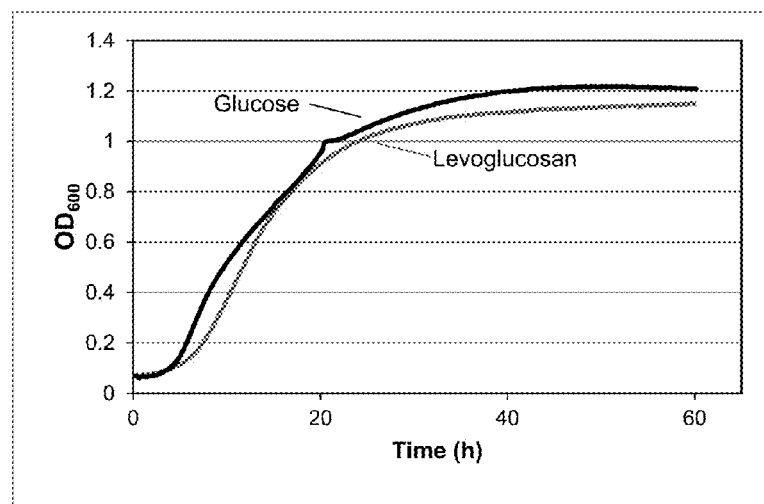
FIG. 2 shows the growth (A and B) and mcl-PHA production (C) of a *P. putida* strain expressing levoglucosan kinase. Glu indicates glucose and LG indicates levoglucosan.
Figure 2:
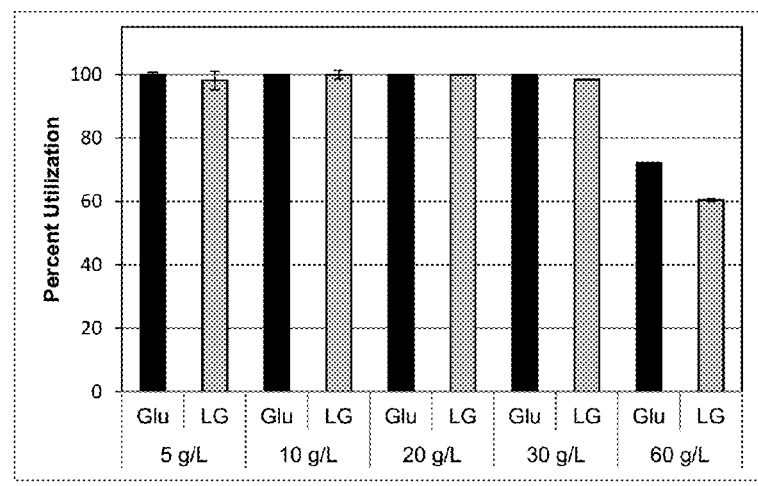
Figure 2:
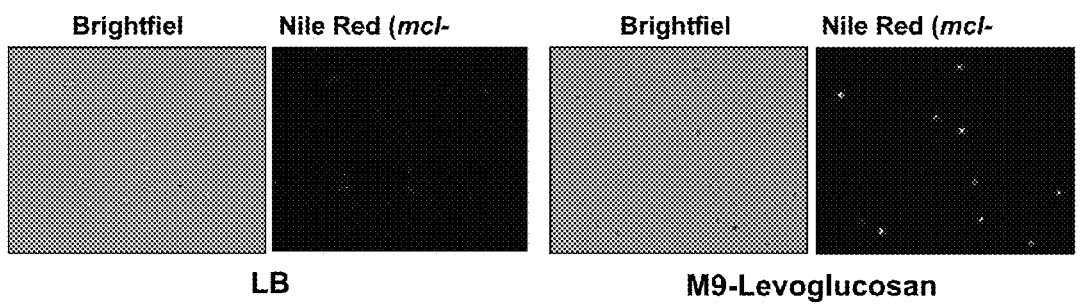

FIG. 2 shows growth, metabolism and polyhydroxyalkanoate production of strain FJPO3. Panel A shows growth curves of FJPO3 in M9 medium supplemented with either 7.5 g/L glucose or 7.5 g/L levoglucosan. Growth profiles in these carbon sources at this concentration are similar, suggesting efficient utilization of levoglucosan in strain FJPO3. Panel B shows that total levoglucosan utilization is similar to glucose utilization and FJPO3 has the capacity to grow at concentrations as high as 60 g/L.

*P. putida* produces medium chain-length polyhydroxyalkanoates (mcl-PHAs), which are high-value polymers that can serve as plastics, adhesive precursors, and as precursors to chemical building blocks or hydrocarbons. As mcl-PHAs represent a potential target to generate from pyrolytic sugars, the generation of mcl-PHAs by *P. putida* using levoglucosan as its sole carbon source as investigated. As shown in Panel C of FIG. 2, Nile Red fluorescence demonstrates that FJPO3 produces mcl-PHAs in N-limited medium [M9 1 mM $(NH_4)_2SO_4$] containing levoglucosan as a sole carbon source, but not in the N- and C-rich LB medium.

Example 2

Media and Growth Conditions

Most growths were in a modified formulation of M9 minimal salts. Briefly, 6.78 g $Na_2PO_4$ (anhydrous), 3 g $KH_2PO_4$, and 0.5 g NaCl were dissolved in 750 mL deionized $H_2O$. The pH was adjusted to 7.4 with 10 N NaOH and brought to 900 mL with $H_2O$. The solution was autoclaved for 15 minutes at 121° C. and allowed to cool. One hundred µL of 1 M $CaCl_2$ (100 µM final) and 2 mL of 1 M $MgSO_4$-$7H_2O$ (2 mM Final), 1 mL of 100 mM $FeSO_4$, (100 µM final) and 10 mL 1 M $(NH_4)_2SO_4$ (10 mM final) was added. In the case of FIG. 2, 1 mM $(NH_4)_2SO_4$, was used to induce mcl-PHA production.

Example 3

Growth Curves and Growth Rate Analysis

Growth curves were generated using a Bioscreen C automated microbiology growth curve analysis system from Growth Curves USA. Overnight cultures were diluted to 0.02 OD in a total volume of 300 µL per well. Incubations were performed at 30° C. with continuous shaking and turbidity measurements ($OD_{420-580}$) were collected every 15 minutes for the duration of the experiments. Spectrophotometric blanks were subtracted from the measured values and each growth curve represents the average of three independent cultures. The maximum specific growth rate ($\mu_{max}$) was calculated as the maximum slope of the log phase of the growth curve over any given 4 hour period during the course of the experiment. In the case of the growths containing β-glucosidases, relevant cultures were spiked with twenty micrograms of agl (*Agrobacterium* sp. β-glucosidase, Megazyme) prior to inoculation in Bioscreen C Honeycomb plates. Plates were held at 40° C. with shaking for 1 hour immediately prior to inoculation.

Example 4

Microscopic Visualization of mcl-PHA Production

One mL of saturated cultures was centrifuged at 5,000×g for 5 minutes. The growth medium was removed via aspiration and the cell pellet was washed twice in phosphate-buffered saline (PBS). Cells were suspended in 100 µL of PBS with 10 µg/mL Nile Red (Molecular Probes, Thermo-Fisher) and incubated for 15 minutes at room temperature in the dark. Cells were centrifuged, washed once in PBS and immobilized on microscope slides by mixing with 1% low-melting-temperature agarose in a 1:1 ratio. Images were acquired using a Nikon Eclipse 80i microscope. Nile Red fluorescence was detected between 560 and 590 nm using band-pass filtering.

Example 5

High Performance Liquid Chromatography

Following the β-glucosidase reaction period, the tubes were placed on ice, filtered through a 0.2 µm filter and analyzed via High-Performance Liquid Chromatography (HPLC; Agilent 1100 series system (Agilent USA, Santa Clara, Calif.)) using a Shodex SP0810 carbohydrate column with de-ashing guard cartridges (BioRad Laboratories, Hercules, Calif.) run at 85° C. with ultra-pure water as the isocratic mobile phase at a flow rate of 0.6 mL/min. A refractive index detector was used for compound detection. By-products were identified by co-elution at the same retention time with pure compounds. Standard curves for substrate (cellobiosan) and products (glucose and levoglucosan) were also generated in order to quantify results. Additionally, enzymes were analyzed via HPLC in buffer alone (without cellobiosan) to ensure no carry-over products inherent to the enzyme preparations.

Example 6

β-Glucosidase Mediated Cleavage of Cellobiosan

The enzymes listed in Table 1 below were used in the cellobiosan cleavage reactions.

TABLE 1

Tested β-glucosidases

| Enzyme | Organism | GH Family | GenBank Accession No. | Seq ID No. |
|---|---|---|---|---|
| bgl1 | *A. niger* | GH3 | AJ132386 | SEQ ID NO: 3 |
| bgl1A | *P. chrysosporium* | GH3 | AAC26489 | SEQ ID NO: 4 |
| bglA | *T. maritima* | GH1 | CAA52276.1 | SEQ ID NO: 5 |
| abg | *Agrobacterium* sp. | GH1 | AAA22085.1 | SEQ ID NO: 6 |

Each reaction was set up in 1.5 mL microcentrifuge tubes using cellobiosan at a concentration of 2 mg/mL in the following buffers: 50 mM sodium maleate, pH 6.5 (*T. maritima* and *Agrobacterium* sp.), and 100 mM sodium acetate, pH 5.0 (*P. chrysosporium* and *A. niger*). For each reaction, 2.5 to 20 µg of enzyme was loaded and the total reaction volume was 400 µL. An additional enzyme-free reaction was run simultaneously to ensure cellobiosan cleavage was enzyme-dependent. Reactions were incubated at 40° C. using a dry-block for 90 minutes. In a separate reaction evaluating the substrate concentration, 0.125 µM of purified *A. niger* β-glucosidase was incubated at 40° C. in a 96-well microtiter plate with 0, 0.5, 1, 2, 4, 8, 16 or 32 mM cellobiose or cellobiosan. Reactions were initiated by the addition of enzyme and quenched by boiling in a thin walled PCR tube at 0.5, 1, 5 and 10 minutes.

Following the reaction periods, the tubes were placed on ice, filtered through a 0.2 filter and analyzed via High-Performance Liquid Chromatography (HPLC; Agilent1100 series system (Agilent USA, Santa Clara, Calif.)) using a Shodex SP0810 carbohydrate column with de-ashing guard cartridges (BioRad Laboratories, Hercules, Calif.) run at 85° C. with ultra-pure water as the isocratic mobile phase at a flow rate of 0.6 ml $min^{-1}$. A refractive index detector was used for compound detection. By-products were identified by co-elution at the same retention time with pure compounds. Standard curves for substrate (cellobiosan) and products (glucose and levoglucosan) were also generated in order to quantify results. Additionally, enzymes were analyzed via HPLC in buffer alone (without the addition of cellobiosan) to ensure no carry-over products inherent to the enzyme preparations.

Figure 3:
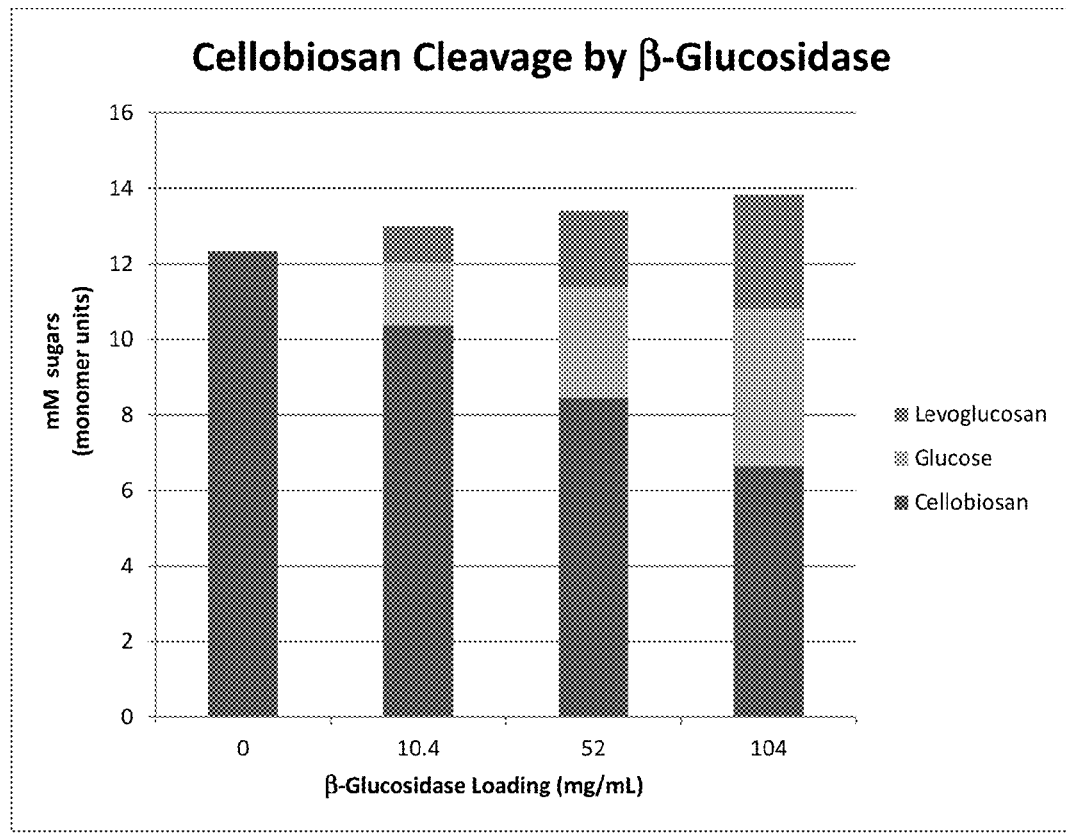
FIG. 3 shows the cleavage of cellobiosan into glucose and levoglucosan increases with the concentration of β-glucosidase enzyme present in the reaction.
Figure 4:
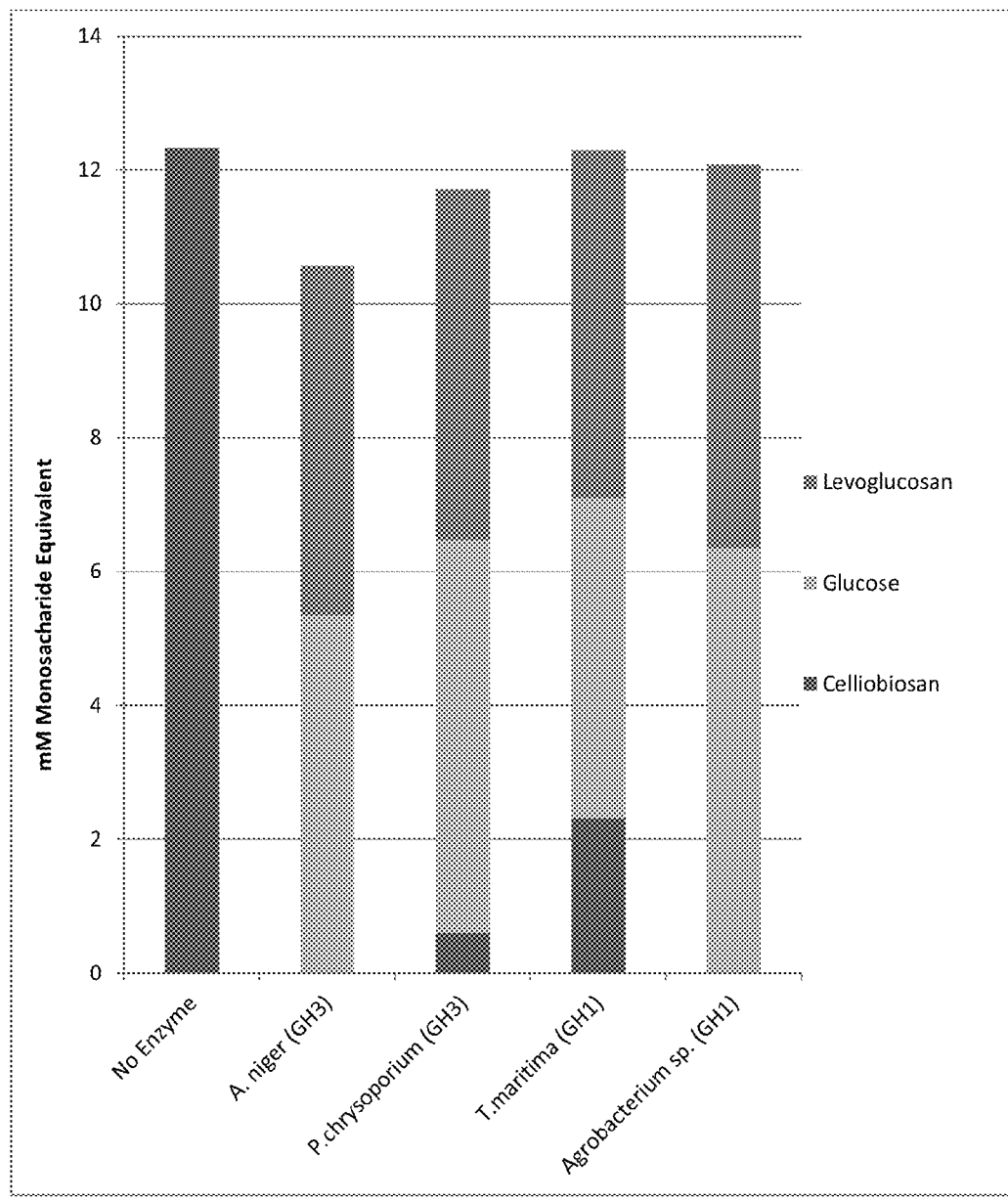
FIG. 4 shows the cleavage of cellobiosan into glucose and levoglucosan by several β-glucosidases. HPLC analysis shows the disappearance of cellobiosan and the appearance of glucose and levoglucosan with the addition of beta-glucosidase enzymes to the reaction. Cellobiosan molarity is reported as double its actual value to represent the molarity of the individual monosaccharide components (glucose plus levoglucosan) for clarity in comparisons.

In order to visualize the data more effectively, numbers were converted to molarity (as depicted in FIGS. 3 and 4). Additionally, cellobiosan molarity numbers were doubled in order to show the total molarity of monosaccharide units. The results of this assay show that β-glucosidases are capable of hydrolyzing the β-1,4-glycosidic bond in cellobiosan to liberate glucose and levoglucosan as products. Additionally, it demonstrates that this activity is conserved from β-glucosidases derived from multiple GH families (GH1 and GH3), derived from both prokaryotic (*Agrobacterium* sp. and *T. maritima*) and eukaryotic organisms (*P. chrysosporium* and *A. niger*), and from mesophilic (*A. niger* and *Agrobacterium* sp.) thermophilic (*P. chrysosporium*) and hyperthermophilic organisms (*T. maritima*).

Figure 5:
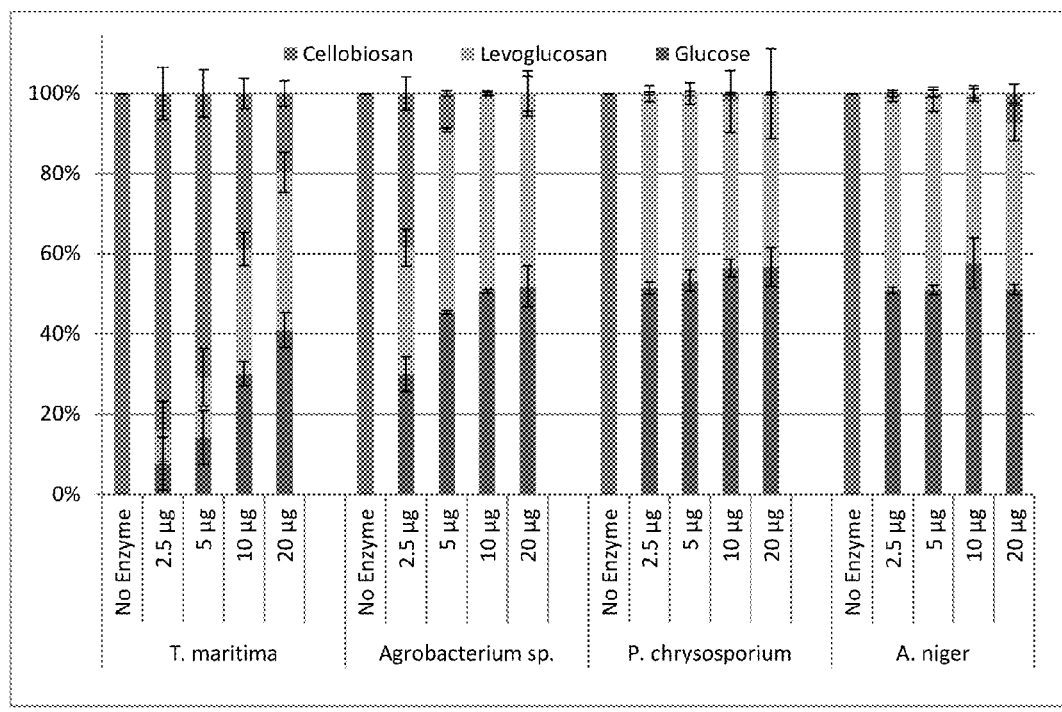
FIG. 5 shows the cleavage of cellobiosan into glucose and levoglucosan by several β-glucosidases at different enzyme loadings.

The exemplary enzymes comprise two representatives each from GH Families 1 and 3 as well as two fungal and two bacterial enzymes: *Aspergillus niger* bgl1 (GH Family 3), *Phanerochaete chrysosporium* bgl1A (GH Family 3, *Thermotoga maritima* bglA (GH Family 1), and *Agrobacterium* sp. abg (GH Family 1). As shown in FIG. 5, all four β-glucosidases are able to cleave cellobiosan to generate glucose and levoglucosan at four different enzyme loadings. HPLC analysis shows the disappearance of cellobiosan and the appearance of glucose and levoglucosan with the addition of beta-glucosidase enzymes to the reaction. Percent utilization is shown wherein the cellobiosan molarity is reported as double its actual value to represent the molarity of the individual monosaccharide components (glucose plus levoglucosan) for clarity in comparisons.

Example 7

β-Glucosidase Enables Growth of *P. Putida*-lgk on Cellobiosan

Figure 6:
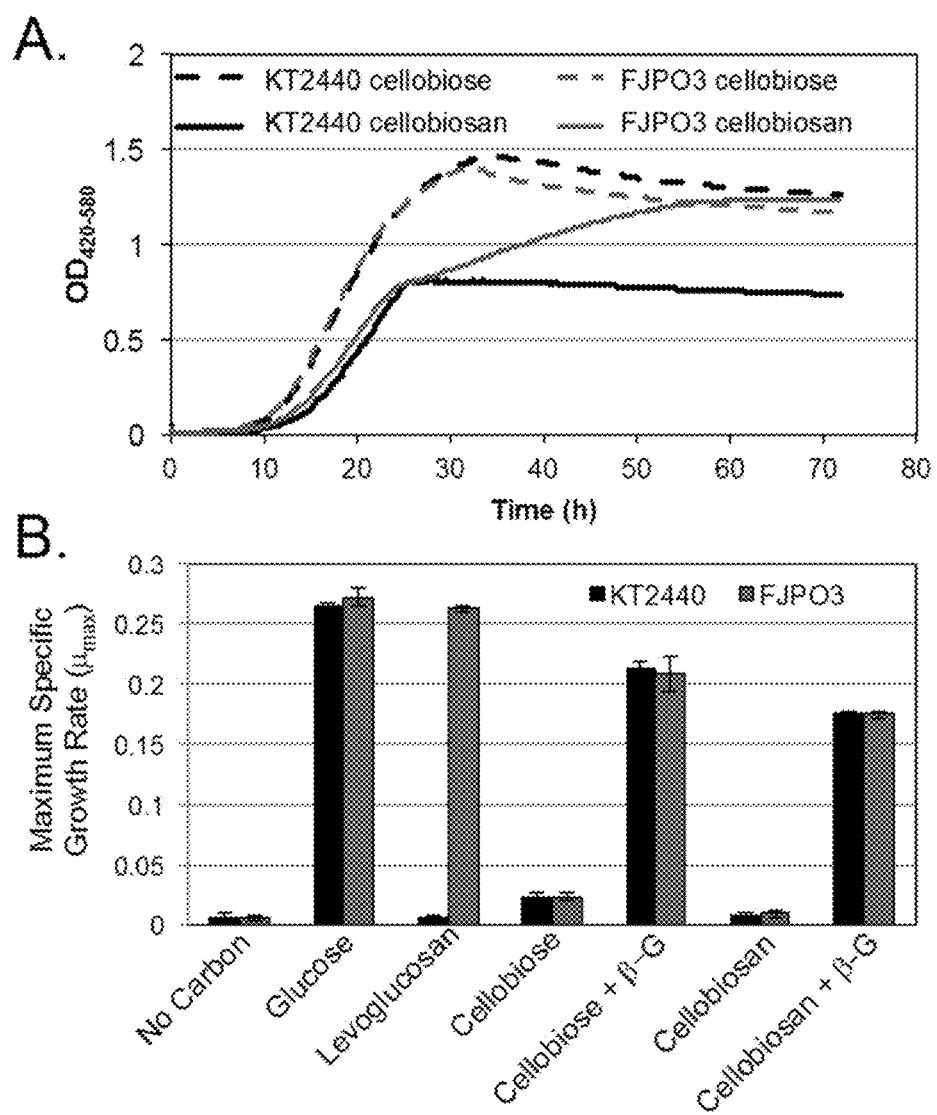
FIG. 6 shows growth of *P. putida* on cellobiose and cellobiosan with or without the addition of exogenous β-glucosidase.
Figure 7:
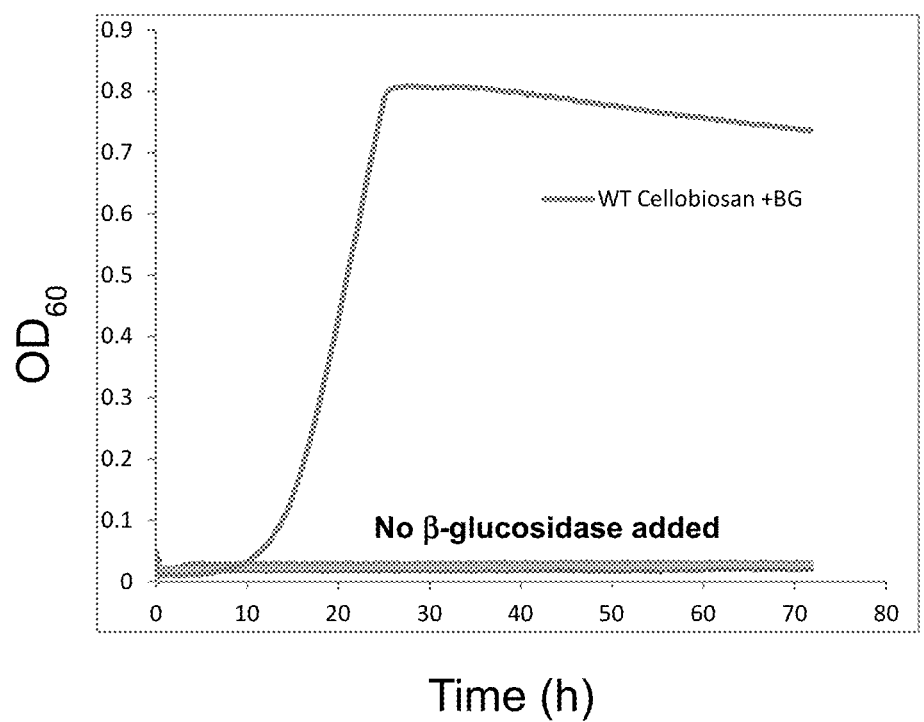
FIG. 7 shows the growth of *P. putida* on cellobiosan with or without the addition of exogenous β-glucosidase.

*P. putida* strains FJPO3 (which expresses the levoglucosan kinase (lgk) gene; see Example 1) and KT2440 were grown using various carbon sources with and without the addition of the *Agrobacterium* sp. abg β-glucosidase As shown in FIG. 6, growth profiles of KT2440 and FJPO3 are virtually indistinguishable in M9 medium containing cellobiose with the addition of abg, demonstrating equivalent glucose usage between the strains (Panel A). Conversely, in the cellobiosan plus abg conditions, while both FJPO3 and KT2440 are capable of utilizing the glucose component of cellobiosan, FJPO3 continues growth at or near the time when KT2440's growth ceases. No growth of either strain was observed in either cellobiose or cellobiosan without the addition of abg. For clarity, these data are not depicted on the growth curves of Panel A. The maximum specific growth rates ($\mu_{max}$) for all conditions are shown in Panel B, along with the max growth rate in M9 media containing levoglucosan and glucose as the sole carbon source.

Example 8

Generation and Fractionation of Pyrolysis Oils

Figure 8:
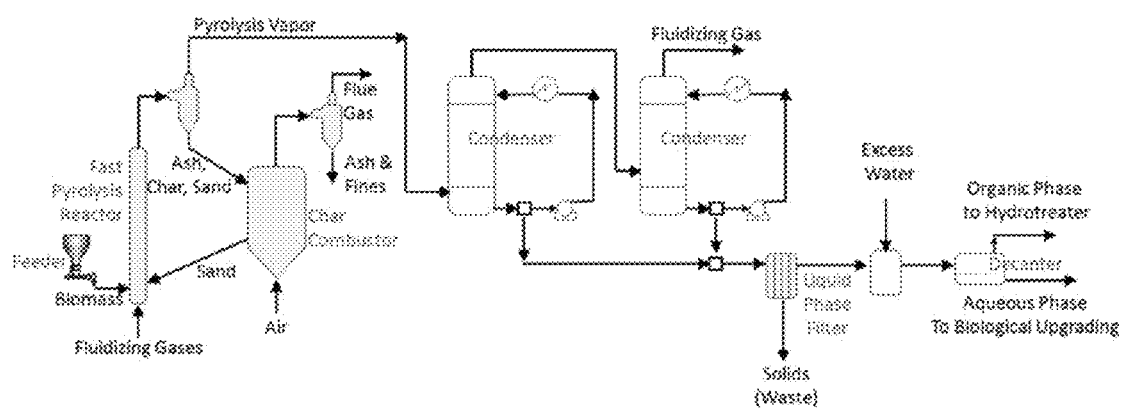
FIG. 8 shows an exemplary pyrolysis scheme.

Pyrolysis oils may be generated by many means, including through the scheme set forth in FIG. 8. Examples can be found in Rover et al., *ChemSusChem* 7:1662-1668 (2014) or Pollard et al., *Journal of Analytical and Applied Pyrolysis* 93:129-138 (2012), among others.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. A method for degrading cellobiosan, comprising contacting a cellobiosan containing material with a microbial β-glucosidase enzyme selected from *Aspergillus niger* β-glucosidase 1 (bgl1), *Phanerochaete chrysosporium* β-glucosidase 1A (bgl1A), *Agrobacterium* sp. β-glucosidase (abg) or *Thermotoga maritima* β-glucosidase (bglA).

2. The method of claim 1, wherein the β-glucosidase enzyme is *Aspergillus niger* β-glucosidase 1 (bgl1) or *Phanerochaete chrysosporium* β-glucosidase 1A (bgl1A).

3. The method of claim 1, wherein the cellobiosan containing material is a pyrolysis oil obtained from biomass.

4. The method of claim 1, wherein the cellobiosan containing material is a fraction obtained by fractionating a pyrolysis oil.

5. The method of claim 4, wherein the pyrolysis oil fraction is an aqueous fraction.

6. A method for producing levoglucosan and glucose from cellobiosan, comprising:
   a) contacting the cellobiosan with at least one microbial β-glucosidase selected from *Aspergillus niger* β-glucosidase 1 (bgl1), *Phanerochaete chrysosporium* β-glucosidase 1A (bgl1A), *Agrobacterium* sp. β-glucosidase (abg) or *Thermotoga maritima* β-glucosidase (bglA),
   b) isolating at least one of the levoglucosan or glucose products.

7. The method of claim 6, wherein the β-glucosidase is *Aspergillus niger* β-glucosidase 1 (bgl1) or *Phanerochaete chrysosporium* β-glucosidase 1A (bgl1A).

8. The method of claim 6, wherein the cellobiosan is contained within a pyrolysis oil obtained from biomass.

9. The method of claim 6, wherein the cellobiosan is contained within a fraction obtained by fractionating a pyrolysis oil.

10. The method of claim 9, wherein the pyrolysis oil fraction is an aqueous fraction.

11. The method of claim 7, wherein the β-glucosidase is *Aspergillus niger* β-glucosidase 1 (bgl1).

12. The method of claim 7, wherein the β-glucosidase is *Phanerochaete chrysosporium* β-glucosidase 1A (bgl1A).

13. The method of claim 6, wherein the β-glucosidase is *Agrobacterium* sp. β-glucosidase (abg) or *Thermotoga maritima* β-glucosidase (bglA).

14. The method of claim 13, wherein the β-glucosidase is *Agrobacterium* sp. β-glucosidase (abg).

15. The method of claim 13, wherein the β-glucosidase is *Thermotoga maritima* β-glucosidase (bglA).

16. The method of claim 2, wherein the β-glucosidase enzyme is *Aspergillus niger* β-glucosidase 1 (bgl1).

17. The method of claim 2, wherein the β-glucosidase enzyme is *Phanerochaete chrysosporium* β-glucosidase 1A (bgl1A).

18. The method of claim 1, wherein the β-glucosidase enzyme is *Agrobacterium* sp. β-glucosidase (abg) or *Thermotoga maritima* β-glucosidase (bglA).

19. The method of claim 18, wherein the β-glucosidase enzyme is *Agrobacterium* sp. β-glucosidase (abg).

20. The method of claim 18, wherein the β-glucosidase enzyme is *Thermotoga maritima* β-glucosidase (bglA).

* * * * *